United States Patent

Gonzenbach et al.

[11] Patent Number: 6,033,649
[45] Date of Patent: Mar. 7, 2000

[54] LIGHT SCREENING AGENTS

[75] Inventors: Hans Ulrich Gonzenbach, Geneva; Gilbert Pittet, Coppet, both of Switzerland

[73] Assignee: Roche Vitamins Inc., Nutley, N.J.

[21] Appl. No.: 08/760,238

[22] Filed: Dec. 4, 1996

[30] Foreign Application Priority Data

Dec. 18, 1995 [EP] European Pat. Off. .............. 95120006
Oct. 8, 1996 [EP] European Pat. Off. .............. 96116083

[51] Int. Cl.⁷ ...................................... A71K 7/42
[52] U.S. Cl. .............................. 424/60; 424/59; 424/400; 424/401; 514/679
[58] Field of Search ................................ 424/59, 60, 401; 514/685, 844, 938, 847, 679; 568/304, 331

[56] References Cited

U.S. PATENT DOCUMENTS

| | | |
|---|---|---|
| 4,387,089 | 6/1983 | DePolo . |
| 5,338,539 | 8/1994 | Raspanti ..................... 424/59 |
| 5,576,354 | 11/1996 | Deflandre et al. . |
| 5,587,150 | 12/1996 | Deflandre et al. . |
| 5,605,679 | 2/1997 | Hansenne et al. . |
| 5,738,842 | 4/1998 | Raspanti et al. ................ 424/59 |

FOREIGN PATENT DOCUMENTS

| | | |
|---|---|---|
| 514 491 | 11/1992 | European Pat. Off. . |
| 667 144 | 1/1995 | European Pat. Off. . |
| 678 292 | 3/1995 | European Pat. Off. . |
| 685 225 | 5/1995 | European Pat. Off. . |
| 685 228 | 5/1995 | European Pat. Off. . |
| 538 431 | 2/1996 | European Pat. Off. . |
| 642 536 | 4/1984 | Switzerland . |
| WO 91/11989 | 8/1991 | WIPO . |

OTHER PUBLICATIONS

SÖFW Journal 122, 8 (1996) 543 seq.
Cosmetics & Toiletries 107, (1982) 45 seq.

*Primary Examiner*—Donna Wortman
*Attorney, Agent, or Firm*—Mark E. Waddell; Stephen M. Haracz; Bryan Cave LLP

[57] ABSTRACT

Photostable, cosmetic light-screening composition, comprising, in a cosmetically acceptable vehicle containing at least one fatty phase, about 0.1 to about 5%, in particular about 1 to about 3% by weight, of a dibenzoylmethane type UV-A screening agent and at least about 0.5%, in particular about 0.5 to about 4.5% by weight, of a $\alpha$-cyano-$\beta,\beta$-diphenyl-acrylate stabilizer, the mole ratio of the acrylate to the dibenzoylmethane derivative being less than 0.8, if the amount of the dibenzoylmethane is 1% or more, and, optionally, at least one conventional UV-B filter.

13 Claims, No Drawings

LIGHT SCREENING AGENTS

FIELD

The invention relates to photostable, cosmetic light-screening compositions for the protection of the human epidermis and the hairs against the ultraviolet rays of wavelengths between 320 and 400 nm, and between 290 and 400 nm respectively.

SUMMARY

In particular, it relates to such compositions which comprise, in a cosmetically acceptable vehicle containing at least one fatty phase, about 0.1 to about 5%, in particular about 1 to about 3% by weight, of a dibenzoylmethane type UV-A screening agent, and at least about 0.5%, in particular about 0.5 to about 4.5% by weight, of a α-cyano-β,β-diphenylacrylate (I) type stabilizer, the mole ratio of the acrylate to the dibenzoylmethane derivative being less than 0.8, if the amount of the dibenzoylmethane is 1% or more, and optionally, at least one UV-B filter.

DETAILED DESCRIPTION

Though the compounds I are themselves effective in absorbing the UV radiation, primarily in the erythemic region (290–320 nm), their present function is to photostabilize the above captioned UV-A-filters.

As far as the UV-A light screening agent is concerned, the preferred compound is 4-tert.butyl-4'-methoxy-dibenzoylmethane, as disclosed, e.g. in U.S. Pat. No. 4,387,089 or CH-Patent 642 536.

Other suitable compounds of this particular type are: 2-methyldibenzoyl-methane, 4-methyl-dibenzoyl-methane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methodydibenzoylmethane.

Examples of suitable compounds I are 2-ethylhexyl-2-cyano-3,3-diphenylacrylate and 2-ethyl-2-cyano-3,3-diphenylacrylate.

The function of the formula I compound is, as pointed out above, to photostabilize the involved UV-A screening agents, i.e. to guarantee a constant protection during prolonged exposure to the UV light. This way, if a repeated application of the cosmetic formulation at various intervals is required, these intervals can be extended.

The present invention relates thus also to a process for stabilizing dibenzoylmethane UV-A screening agents with respect to the UV radiation of wavelengths between 320 and 400 nm, characterised in that about 0.5 to about 4.5% by weight of the stabilizer is added to about 0.1 to 5% by weight of the dibenzoylmethane UV-A screening agent.

The desired stabilization of the material of UV-A filters is easily established by strictly parallel experiments with the respective UV-A filters and the compounds I using an appropriately equipped Xenon lamp as a solar simulator. Irradiated are standard preparations of the investigated products, e.g. solutions in, preferably, higher boiling cosmetic solvents, e.g. deltyl (isopropyl myristate), the resulting sunscreen being spread on glass plates. After the irradiation, the plates are immersed into a suitable solvent (e.g. ethanol) and the UV spectrum is recorded. The stabilizing effect is directly correlated to the difference in absorbance at $\lambda_{max}$ before and after the irradiation. Usually, a combination of UV-A filter and stabilizer as exemplified below is used for the assessment.

Both components of the present combination of the light-screening agents are lipophilic. The cosmetic formulations contain thus at least one fatty phase, and the formulations can consequently present themselves in the form of emulsions, lotions or gels.

Suitably the cosmetic screening composition takes the form of an oil, a lotion, a gel, a solid stick, an emulsion, e.g. cream, milk or of a vesicular dispersion of ionic or nonionic amphiphilic lipids, an aerosol, a spray, a foam, a powder, a shampoo, a hair conditioner or lacquer or a make-up, etc.

The usual solvents known to the skilled practitioner can be used for the preparation of these forms, e.g. oils, waxes, alcohols, polyols, etc. The preferred agents are fatty acids, esters, fatty alcohols, but also ethanol, isopropanol, propylene glycol, glycerine, etc.

The cosmetic formulations may contain further adjuvants, e.g. further solvents, thickeners, emollients, emulsifiers, humectants, tensides, preservatives, antifoams, fragrances, oils, waxes, lower polyols and monohydric alcohols, propellants, silicones, colourings and pigments, etc.

They may also contain—monomeric or polymeric (e.g. polysiloxanes, e.g. EP 538431, polyacrylates, etc.)—UV filter(s). These may be selected from the list according to the desired chemical and physical properties of the formulation, e.g. according to the desired degree of protection, to wavelength, ε max, solubility, stability, or safety, see e.g., SÖFW Journal 122, 8 (1996) 543 seq., Cosmetics & Toiletries 107 (1982) 45 seq.

For protection of the hair, the suitable formulations are shampoos, conditioners, lotions, gels, emulsions, dispersions, lacquers, etc.

The preparation of all these formulations is well known to the skilled artisan in this field.

As still further suitable UV-B filters, microfine pigments, such as the usual micropigments of metal oxides may be used. Particularly in case of emulsions, such UV filters may, naturally, also be water-soluble derivatives. Suitable amounts of the UV-B filter are ca. 1–ca. 12%.

The most important advantage of the novel stabilizer stems from the low dosage of the novel stabilizer—which dosage can be considerably smaller than the dosages of the UV-A filter used—the practical user is thus completely free in the choice regarding the material used for the filtration of the UV-B rays.

In this respect, the novel stabilization is superior to the particular way of stabilization as disclosed in EP 514 491 B1, and this for the following reason:

According to this known process, a ratio of compound I to dibenzoylmethane being not less than 0.8 is compulsory, which ratio narrows the possibilities in the means of achieving the absorption of the UV light over the total range, resulting in the so-called total block.

Convenient couples of dibenzoyl methane derivatives and acrylates are as follows:

| dibenzoyl methane | compound I |
|---|---|
| 1 | 0.5 |
| 1 | 0.9 |
| 1.5 | 1 |
| 2 | 1 |
| 2 | 1.5 |
| 2.5 | 1.5 |
| 2.5 | 2 |
| 3 | 2 |
| 3 | 2.5 |

EXAMPLES

The following compositions were prepared:

| | | % W/W |
|---|---|---|
| | O/W SUNSCREEN LOTION 1 | |
| A) | Glyceryl mono myristate | 4.0 |
| | Cetyl alcohol | 1.0 |
| | Coco-caprylate/caprate | 10.0 |
| | (Mixture of esters of coconut alcohol and n-octanoic acid and n-decanoic acid) (sold under trade name CETIOL LC by Henkel) | |
| | Butyl methoxy dibenzoylmethane | 1.0 |
| | (1-[4-(1,1-dimethylethyl)phenyl]-3-(4-methoxyphenyl)-1,3-propandione) (sold under the trade name PARSOL 1789 by GIVAUDAN-ROURE S.A.) | |
| | Octocrylene | 0.9 |
| | (2-Ethylhexyl-2-cyano-3,3-diphenylacrylate, sold under the trade name UVINUL N-539 by BASF) | |
| | Mixture of parabens in phenoxy ethanol | 0.6 |
| | Potassium cetyl phosphate (potassium salt of hexadecyl phosphate) (sold under the trade name AMPHISOL K by Givaudan-Roure S.A.) | 2.0 |
| | EDTA Na2 | 0.1 |
| B) | Deionized water | 64.95 |
| | Carbomer (1% dispersion in water, homopolymer of acrylic acid crosslinked with an allyl ether of sucrose) (sold under the trade name Carbopol 980 by B. F. Goodrich) | 10.0 |
| | Propylene glycol | 5.0 |
| C) | Potassium hydroxyde, 10% solution | 0.45 |
| | | 100.00 |
| | O/W SUNSCREEN LOTION 2 | |
| A) | Glyceryl mono myristate | 4.0 |
| | Cetyl alcohol | 1.0 |
| | Coco-caprylate/caprate | 10.0 |
| | Butyl methoxy dibenzoylmethane | 2.0 |
| | Octocrylene | 1.5 |
| | Mixture of parabens in phenoxy ethanol | 0.6 |
| | Potassium cetyl phosphate (potassium salt of hexadecyl phosphate) | 2.0 |
| | EDTA Na2 | 0.1 |
| B) | Deionized water | 63.35 |
| | Carbomer (1% dispersion in water, homopolymer of acrylic acid crosslinked with an allyl ether of sucrose) | 10.0 |
| | Propylene glycol | 5.0 |
| C) | Potassium hydroxyde, 10% solution | 0.45 |
| | | 100.00 |
| | O/W SUNSCREEN LOTION 3 | |
| A) | Glyceryl mono myristate | 4.0 |
| | Cetyl alcohol | 1.0 |
| | Coco-caprylate/caprate | 10.0 |
| | Butyl methoxy dibenzoylmethane | 3.0 |
| | Octocrylene | 2.5 |
| | Mixture of parabens in phenoxy ethanol | 0.6 |
| | Potassium cetyl phosphate (potassium salt of hexadecyl phosphate) | 2.0 |
| | EDTA Na2 | 0.1 |
| B) | Deionized water | 61.35 |
| | Carbomer (1% dispersion in water, homopolymer of acrylic acid crosslinked with an allyl ether of sucrose) | 10.0 |
| | Propylene glycol | 5.0 |
| C) | Potassium hydroxyde, 10% solution | 0.45 |
| | | 100.00 |

We claim:

1. A photostable, cosmetic light-screening composition, comprising, in a cosmetically acceptable vehicle containing at least one fatty phase, about 0.1 to about 5% of a dibenzoylmethane derivative UV-A screening agent and at least 0.5%, by weight, of an α-cyano-β,β-diphenyl-acrylate stabilizer, the mole ratio of the stabilizer to the UV-A screening agent being less than 0.8, when the amount of the UV-A screening agent is 1% or more.

2. The composition according to claim 1, wherein the UV-A screening agent is present in an amount of about 1 to about 3% by weight.

3. The composition according to claim 1, wherein the stabilizer is present in an amount of about 0.5 to about 4.5% by weight.

4. The composition of claim 1, further comprising at least one UV-B filter.

5. The composition according to claim 1, wherein the stabilizer is 2-ethylhexyl-2-cyano-3,3-diphenyl-acrylate or ethyl-2-cyano-3,3-diphenyl-acrylate.

6. The composition according to claim 1, wherein the UV-A screening agent is selected from the group consisting of: 2-methyldibenzoylmethane, 4-methyl-dibenzoyl-methane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoylmethane.

7. The composition according to claim 1, wherein the UV-A screening agent is 4-tert-butyl-4'-methoxydibenzoylmethane.

8. The composition according to claim 1, wherein said composition is in the form of an oil, a lotion, a gel, a solid stick, an emulsion, an aerosol, a spray, a foam, a powder, a shampoo, a hair conditioner or lacquer or a make-up.

9. The composition according to claim 1, further comprising a cosmetic adjuvant which is selected from the group consisting of solvents, thickeners, emollients, emulsifiers, humectants, tensides, preservatives, antifoams, fragrances, oils, waxes, lower polyols and monohydric alcohols, propellants, silicones, colorings and pigments.

10. The composition according to claim 4, wherein the UV-A screening agent is present in an amount of about 0.1 to about 5%, the stabilizer is present in an amount of about 0.5 to about 4.5%, and the UV-B-filter is present in an amount of about 1 to about 12% by weight.

11. A process for the protection of the human epidermis or hairs against the damaging action of the UV radiation of wavelengths between 290 and 400 nm, which comprises applying to the skin or the hairs an effective light screening quantity of the cosmetic light-screening composition of claim 1.

12. A process for stabilizing dibenzoylmethane UV-A screening agents with respect to UV radiation of wavelengths between 320 and 400 nm, which comprises adding about 0.5 to about 4.5% by weight of the stabilizer defined in claim 1 to about 0.1 to about 5% by weight of the UV-A screening agent, the mole ratio of the stabilizer to the UV-A screening agent being less than 0.8 when the amount of the UV-A screening agent is 1% or more.

13. The composition according to claim 8, wherein the emulsion is a cream, milk or a vesicular dispersion of ionic or nonionic amphiphilic lipids.

* * * * *